United States Patent [19]

Gehring et al.

[11] Patent Number: 4,877,439

[45] Date of Patent: Oct. 31, 1989

[54] HERBICIDAL 1-ARYLPYRAZOLES, COMPOSITIONS AND USE

[75] Inventors: Reinhold Gehring, Wuppertal; Otto Schallner, Monheim; Jörg Stetter, Wuppertal; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 210,607

[22] Filed: Jun. 23, 1988

[30] Foreign Application Priority Data

Jul. 2, 1987 [DE] Fed. Rep. of Germany ....... 3721868

[51] Int. Cl.$^4$ .......................... A01N 57/02; C07F 9/65
[52] U.S. Cl. ........................................... 71/86; 71/71; 71/87; 546/22; 548/119
[58] Field of Search .................. 546/22; 548/119, 362; 71/86, 87

[56] References Cited

U.S. PATENT DOCUMENTS 4,363,804 12/1982 Fancher ............................ 548/119

4,614,533 9/1986 Schallner et al. ...................... 71/92

Primary Examiner—Robert W. Ramsuer
Attorney, Agent, or Firm—Sprung Horn Kramer & Woods

[57] ABSTRACT

Herbicidal 1-arylpyrazoles of the formula

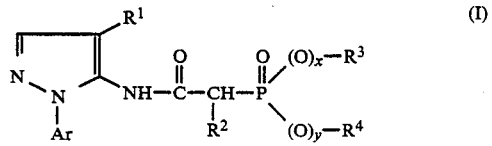

in which
- R$^1$ represents hydrogen or nitro,
- R$^2$ represents hydrogen or alkyl,
- R$^3$ and R$^4$ independently of one another each represent alkyl, halogenoalkyl or optionally substituted aryl,
- Ar represents optionally substituted phenyl or optionally substituted pyridyl,
- x represents a number 0 or 1 and
- y represents a number 0 or 1.

12 Claims, No Drawings

HERBICIDAL 1-ARYLPYRAZOLES, COMPOSITIONS AND USE

The invention relates to new 1-arylpyrazoles, a process for their preparation and their use as herbicides.

It has already been disclosed that certain 1-arylpyrazoles such as, for example, 4-nitro-5-propionamido-1-(2,6-dichloro-4-trifluoromethyl-phenyl)-pyrazole possess herbicidal properties (compare EP 154,115).

However, the herbicidal activity of these previously known compounds towards problem weeds is not completely satisfactory in all areas of application, neither is their toleration by important cultivated plants.

New 1-arylpyrazoles of the general formula (I)

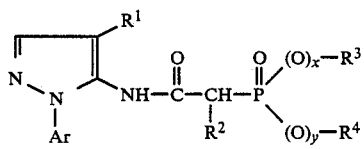

in which
$R^1$ represents hydrogen or nitro,
$R^2$ represents hydrogen or alkyl,
$R^3$ and $R^4$ independently of one another each represent alkyl, halogenoalkyl or optionally substituted aryl,
Ar represents optionally substituted phenyl or optionally substituted pyridyl,
x represents a number 0 or 1 and
y represents a number 0 or 1, have been found.

Furthermore, it has been found that the new 1-arylpyrazoles of the general formula (I),

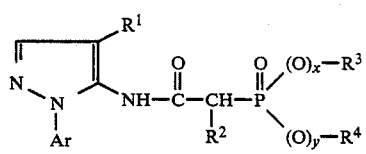

in which
$R^1$ represents hydrogen or nitro,
$R^2$ represents hydrogen or alkyl,
$R^3$ and $R^4$ independently of one another each represent alkyl, halogenoalkyl or optionally substituted aryl,
Ar represents optionally substituted phenyl or optionally substituted pyridyl,
x represents a number 0 or 1 and
y represents a number 0 or 1,
are obtained when 5-halogenoalkanoylamido-1-arylpyrazoles of the formula (II)

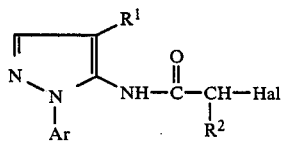

in which
Hal represents halogen and
$R^1$, $R^2$ and Ar have the abovementioned meaning, are reacted with phosphorus compounds of the formula (III),

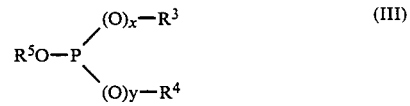

in which
$R^5$ represents alkyl and
$R^3$, $R^4$, x and y have the abovementioned meaning, if desired in the presence of a diluent and if desired in the presence of a reaction auxiliary.

Finally, it has been found that the new 1-arylpyrazoles of the general formula (I) possess good herbicidal properties, including in particular selective herbicidal properties.

Surprisingly, the 1-arylpyrazoles of the general formula (I) according to the invention simultaneously show, in addition to a clearly improved herbicidal activity towards problem weeds, a considerably improved crop plant selectivity, in comparison to the 1-arylpyrazoles known from the prior art, such as, for example, 4-nitro-5-propionamido-1-(2,6-dichloro-4-trifluoromethylphenyl)pyrazole, which are similar compounds chemically and with respect to their action.

Formula () provides a general definition of the 1-arylpyrazoles according to the invention. Preferred compounds of the formula (I) are those in which
$R^1$ represents hydrogen or nitro,
$R^2$ represents hydrogen or straight-chain or branched alkyl having 1 to 4 carbon atoms,
$R^3$ and $R^4$ independently of one another each represent straight-chain or branched alkyl having 1 to 4 carbon atoms, straight-chain or branched halogenoalkyl having 1 to 4 carbon atoms and 1 to 9 identical or different halogen atoms, or phenyl which is optionally monosubstituted or polysubstituted by identical or different substituents, suitable phenyl substituents being: halogen, nitro, and in each case straight-chain or branched alkyl or halogenoalkyl, each having 1 to 4 carbon atoms and in the case of halogenoalkyl having 1 to 9 identical or different halogen atoms,
Ar represents phenyl, 2-pyridyl, 3-pyridyl or 4-pyridyl, which are each optionally monosubstituted or polysubstituted by identical or different substituents, suitable substituents being in each case: cyano, nitro, halogen, alkyl, alkoxy or alkoxycarbonyl which are each straight-chain or branched and each have 1 to 4 carbon atoms, in each case straight-chain or branched halogenoalkyl or halogenoalkoxy, each having 1 to 4 carbon atoms and 1 to 9 identical or different halogen atoms or a radical —S(O)$_z$-R$^6$
in which
$R^6$ represents amino, alkyl, alkylamino, dialkylamino or halogenoalkyl, each being straight-chain or branched and having 1 to 4 carbon atoms in the individual alkyl parts and in the case of halogenoalkyl having 1 to 9 identical or different halogen atoms,
x represents a number 0 or 1,
y represents a number 0 or 1 and
z represents a number 0, 1 or 2.

Particularly preferred compounds of the formula (I) are those in which
$R^1$ represents hydrogen or nitro,
$R^2$ represents hydrogen, methyl or ethyl,
$R^3$ and $R^4$ independently of one another each represent methyl, ethyl, n- or i-propyl, n-, i-, s- or t-butyl, chloromethyl, chloroethyl, chloropropyl, bromomethyl, bromoethyl, bromopropyl, dichloromethyl, trichloroethyl, trifluoroethyl, pentafluoroethyl or trichloromethyl, or phenyl which is optionally monosubstituted, disubstituted or trisubstituted by identical or different substituents, suitable phenyl substituents being: fluorine, chlorine, bromine, nitro, methyl, ethyl, n- or i-propyl or trifluoromethyl, Ar represents phenyl which is optionally monosubstituted to pentasubstituted by identical or different substituents, or 2-pyridyl, which is optionally monosubstituted to tetrasubstituted by identical or different substituents, suitable phenyl and pyridyl substituents being in each case: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical $-S(O)_z-R^6$ in which $R^6$ represents amino, methylamino, ethylamino, dimethylamino, diethylamino, fluorodichloromethyl, difluoromethyl, tetrafluoroethyl, trifluorochloroethyl, trichloromethyl, trichloroethyl, trifluoromethyl, methyl or ethyl, x represents a number 0 or 1, y represents a number 0 or 1 and z represents a number 0, 1 or 2.

Very particularly preferred compounds of the formula (I) are those in which $R^1$ represents nitro, $R^2$ represents hydrogen, $R^3$ and $R^4$ independently of one another each represent methyl, ethyl, n- or i-propyl or phenyl;

Ar represents phenyl which is optionally monosubstituted to pentasubstituted by identical or different substituents, suitable substituents being: fluorine, chlorine, bromine, methyl, ethyl, methoxy, ethoxy, trifluoromethyl, trifluoromethoxy, trifluoromethylthio, trifluoromethylsulphinyl or trifluoromethylsulphonyl, x represents a number 0 or 1 and y represents the number 1.

If, for example, 5-chloroacetamido-4-nitro-1-(2,6-dichloro-4-trifluoromethylphenyl)-pyrazole and triethyl phosphite are used as starting materials, then the course of the reaction of the process according to the invention can be represented by the following equation:

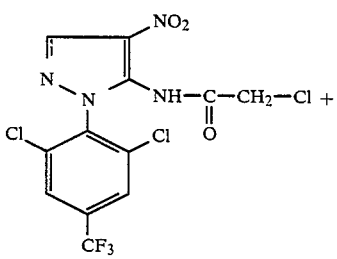

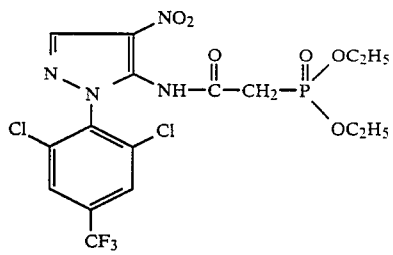

Formula (II) provides a general definition of the 5-halogenoalkanoylamido-1-aryl-pyrazoles required as starting materials for carrying out the process according to the invention. In this formula (II), $R^1$, $R^2$ and Ar preferably represent those radicals which have already been mentioned as preferred for these substituents in connection with the description of the substances of the formula (I) according to the invention. Hal preferably represents chlorine or bromine.

The 5-halogenoalkanoylamido-1-arylpyrazoles of the formula (II) are known or can be prepared analogously to known processes (compare, for example, EP 154,115).

Formula (III) provides a general definition of the phosphorus compounds furthermore required as starting materials for carrying out the process according to the invention. In this formula (III), $R^3$, $R^4$, x and y preferably represent those radicals and indices which have already been mentioned as preferred for these substituents and indices in connection with the description of the substances of the formula (I) according to the invention. $R^5$ preferably represents straight-chain or branched alkyl having 1 to 4 carbon atoms, in particular methyl or ethyl.

The phosphorus compounds of the formula (III) are generally known compounds of organic chemistry (compare, for example, Houben-Weyl "Methoden der organischen Chemie" ["Methods of organic chemistry"] 4th edition; volume 12/1 p. 208 et seq. and also p. 324 et seq. and volume 12/2 p. 53 et seq; Thieme Verlag Stuttgart 1963/1964).

If desired, the process according to the invention can be carried out in the presence of a suitable diluent. Those which are particularly suitable are the customary inert organic solvents. Preferably, however, the reaction is carried out without the addition of solvents, using a suitable excess of phosphorus compound of the formula (III), which is simultaneously employed as the diluent.

If desired, the process according to the invention can be carried out in the presence of a suitable reaction auxiliary. Those which are preferably used are alkyl halides whose alkyl radical corresponds to the radical $R^5$ which is set free in the reaction according to the invention as the compound of the formula (IV)

$$R^5-Hal \qquad (IV)$$

in which $R^5$ and Hal have the abovementioned meaning.

The reaction temperatures can be varied within a relatively wide range when carrying out the process according to the invention. In general, the reaction is carried out at temperatures between 20° C. and 200° C., preferably at temperatures between 50° C. and 150° C.

For carrying out the process according to the invention, 1.0 to 10.0 mols, preferably 1.0 to 3.0 mols, of phosphorus compound of the formula (III) and if appropriate 0.01 to 1.0 mol, preferably 0.1 to 0.2 mol, of reaction auxiliary are generally employed per mol of 5-halogenoalkanoylamido-1-aryl-pyrazole of the formula (II). Performance of the reaction work-up and isolation of the reaction products are effected by generally customary methods (compare Houben-Weyl "Methoden der organischen Chemie" ["Methods of organic chemistry"] volume 12/1 p. 433 et seq.; 4th edition, Thieme Verlag Stuttgart 1963 and also the preparation examples).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used here with particularly good success for selectively combating dicotyledon weeds in monocotyledon and dicotyledon cultures, such as, for example, cotton, wheat or rice. Moreover, at suitable application rates the active compounds according to the invention also show growth regulatory actions and can be used, for example, as cotton defoliants.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compounds, and very fine capsules in polymeric substances.

These formulations are produced in known manner, for example by mixing the active compounds with extenders, that is, liquid solvents, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salt and ground natural minerals, such as kaolins, clays, talc, chalk, quartz, attapulgite, montmorillonite or diatomaceous earth, and ground synthetic minerals, such as highly-disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use dyestuffs such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beets, and 4-amino-6-(1,1-dimethylethyl)-3-methylthio-1,2,4-triazin-5(4H)-one for combating weeds in soy beans. Mixtures with 2,4-dichlorophenoxyacetic acid; 2,4-dichlorophenoxypropionic acid; 4-(2,4-dichlorophenoxy)-butyric acid; (2-methyl-4-chlorophenoxy)-acetic acid; (4-chloro-2-methylphenoxy)-propionic acid; 3,5,6-trichloro-2-pyridyloxyacetic acid; 2-{4-[(6-chloro-2-benzoxazolyl)-oxy]-phenoxy}-propanoic acid, its methyl or its ethyl ester; (trimethylsilylmethyl) 2-[4-(3,5-dichloropyrid-2-yloxy)-phenoxy]-propionate; 3,6-dichloro-2-pyridine carboxylic acid; 1-(3-trifluoromethyl-phenyl)-4-methylamino-5-chloro-6-pyridazone; N-(methoxymethyl)-2,6-diethylphenylchloroacetamide; N-(butoxymethyl)-2-chloro-N-(2,6-diethylphenyl)-acetamide; 2-chloro-N-(2,6-dimethylphenyl)-N-[(1H)-pyrazol-1-yl-methyl]-acetamide; 2-ethyl-6-methyl-N-(1-methyl-2-methoxyethyl)-chloroacetanilide; α-chloro-2',6'-diethyl-N-(2-propoxyethyl)-acetanilide; 2-chloro-N-isopropylacetanilide; 4-(di-n-propylamino)-3,5-dinitrobenzenesulphonamide; N-(1-ethylpropyl)-3,4-dimethyl-2,6-dinitroaniline; 2,6-dinitro-4-trifluoromethyl-N,N-dipropylaniline; methyl 5-(2,4-dichlorophenoxy)-2-nitrobenzoate; N,N-dimethyl-N'-(3-chloro-4-methylphenyl)-urea; N,N-dimethyl-N'(3-trifluoromethylphenyl)-urea; N,N-dimethyl-N'-(4-isopropylphenyl)-urea; methyl 2-[4,5-dihydro-4-methyl-4-(1-methylethyl)-5-oxo-1H-imidazol-2-yl]-4(5)-methylbenzoate; 3,5-dibromo-4-hydroxy-benzonitrile; 3,5-diiodo-4-hydroxybenzonitrile; N-methyl-2-(1,3-benzothiazol-2-yloxy)-acetanilide; methyl 2-[[[[[(4,6-dimethoxypyrimidin-2-yl)-amino]-carbonyl]-amino]-sulphonyl]-methyl]-benzoate; ethyl 2-{[[(4-chloro-6-methoxy-2-pyrimidinyl)-aminocarbonyl]-aminosulphonyl}-benzoate; 2-chloro-N-{[(4-methoxy-6-methyl-1,3,5-triazin-2-yl)-amino]-carbonyl}-benzenesulphonamide; 2-{[[((4-methoxy-6-methyl-1,3,5-triazin-2-yl)-amino)-carbonyl]-amino]-sulphonyl}-benzoic acid or its methyl ester; methyl 2-{[(4,6-dimethyl-2-pyrimidinyl)-aminocarbonyl]-aminosulphonyl}-benzoate; methyl 3-[[[[(4-methoxy-6-methyl-1,3,5-triazin-2-yl)-amino]-carbonyl]-amino]-sulphonyl]-thiophene-2-carboxylate; N,S-diethyl-N-cyclohexylthiolcarbamate; S-ethyl N,N-di-n-propyl-thiocarbamate; S-ethyl-N,N-hexamethylene-thiolcarbamate; S-[(4-chlorophenyl)-methyl]-N,N-diethyl-thiocarbamate; N,N-diisopropyl-S-(2,3,3-trichloroallyl)-thiolcarbamate; 2-chloro-4-ethylamino-6-isopropylamino-1,3,5-triazine; 2-chloro-4-ethylamino-6-(3-cyanopropylamino)-1,3,5-triazine; 2,4-bis-[N-ethylamino]-6-methylthio-1,3,5-triazine; 4-ethylamino-2-t-butylamino-6-methylthio-s-triazine; 4-amino-6-t-butyl-3-ethylthio-1,2,4-triazin-5(4H)-one; 3-isopropyl-2,1,3-benzothiadiazin-4-one-2,2-dioxide; exo-1-methyl-4-(1-methylethyl)-2-(2-methylphenyl-methoxy)-7-oxabicyclo-(2,2,1)-heptane or 1-methyl-3-phenyl-5-(3-trifluoromethylphenyl)-4-pyridone are also possible.

Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and the use of the active compounds according to the invention can be seen from the following examples.

PREPARATION EXAMPLES

EXAMPLE 1

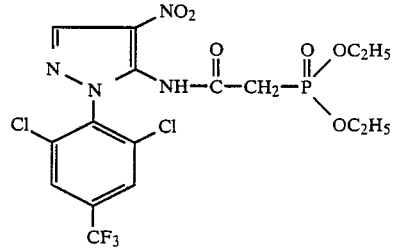

8.2 g (0.02 mol) of 5-chloroacetamido-1-(2,6-dichloro-4-trifluoromethylphenyl)-4-nitro-pyrazole (compare EP 154,115) and 6.8 ml (0.04 mol) of triethyl phosphite are slowly heated to 120° C. Above about 100° C., a vigorous evolution of gas takes place. The mixture is stirred for 2 hours at 120° C. and excess triethyl phosphite is then removed by distillation in vacuo, and the residue is purified by column chromatography (silica gel; dichloromethane/acetone 9:1).

4.6 g (44% of theory) of 5-(O,O-diethyl-phosphonylacetamido)-1-(2,6-dichloro-4-trifluoromethylphenyl)-4-nitro-pyrazole of melting point 158° C.–161° C. are obtained.

EXAMPLE 2

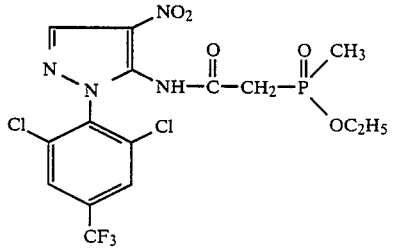

8.2 g (0.02 mol) of 5-chloroacetamido-1-(2,6-dichloro-4-trifluoromethylphenyl)-4-nitro-pyrazole and 6 ml (0.04 mol) of diethyl methylphosphonate are slowly heated to 100° C. From about 90° C., gas evolution begins. The mixture is stirred for 10 minutes at 100° C. and excess methylphosphonate is then removed by distillation in vacuo, and the residue is purified by column chromatography (silica gel; dichloromethane/acetone 9:1).

3.3 g (34% of theory) of 5-(O-ethylmethylphosphinoylacetamido)-1-(2,6-dichloro-4-trifluoromethylphenyl)-4-nitro-pyrazole of melting point 128° C. (decomp.) are obtained.

The following 1-arylpyrazoles of the general formula (I)

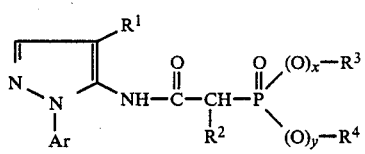

are obtained in a corresponding manner and according to the general instructions for preparation:

| Ex. No. | $R^1$ | $R^2$ | $\overset{O}{\underset{-P}{\parallel}}\diagup^{(O)_x-R^3}_{(O)_y-R^4}$ | Ar | Melting point/°C. |
|---|---|---|---|---|---|
| 3 | $NO_2$ | H | $\overset{O}{\underset{-P}{\parallel}}\diagup^{OCH_3}_{OCH_3}$ | 2,6-Cl, 4-CF$_3$-phenyl | 208 |
| 4 | $NO_2$ | H | $\overset{O}{\underset{-P}{\parallel}}\diagup^{OC_2H_5}_{OC_2H_5}$ | 2,3,6-Cl, 4-CF$_3$-phenyl | 127 |
| 5 | $NO_2$ | H | $\overset{O}{\underset{-P}{\parallel}}\diagup^{OCH_3}_{OCH_3}$ | 2,3,6-Cl, 4-CF$_3$-phenyl | 125 |
| 6 | $NO_2$ | H | $\overset{O}{\underset{-P}{\parallel}}\diagup^{CH_3}_{OC_2H_5}$ | 2,3,6-Cl, 4-CF$_3$-phenyl | 167 |

USE EXAMPLES

The compound shown below was employed as comparison substance in the following use examples:

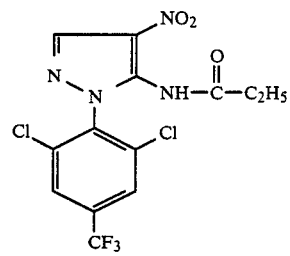

5-Propionamido-4-nitro-1-(2,6-dichloro-4-trifluoromethylphenyl)-pyrazole (known from EP 154,115).

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient here to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compounds according to the following preparation Examples 1, 2, 3, 5 and 6 show a clear superiority in activity and also in useful plant selectivity compared to the prior art.

It is understood that the specification and examples are illustrative but not limitative of the present invention and that other embodiments within the spirit and scope of the invention will suggest themselves to those skilled in the art.

We claim:
1. A 1-arylpyrazole of the formula

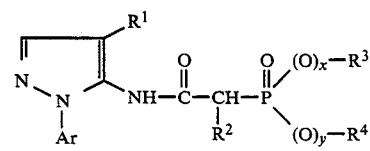

in which
$R^1$ represents hydrogen or nitro,
$R^2$ represents hydrogen or alkyl,
$R^3$ and $R^4$ independently of one another each represent alkyl, halogenoalkyl or optionally substituted aryl,
Ar represents optionally substituted phenyl or optionally substituted pyridyl,
x represents a number 0 or 1 and
y represents a number 0 or 1.
2. A 1-arylpyrazole according to claim 1, in which $R^1$ represents hydrogen or nitro, R² represents hydrogen or straight-chain or branched alkyl having 1 to 4 carbon atoms, R³ and R⁴ independently of one another each represent straight-chain or branched alkyl having 1 to 4 carbon atoms, straight-chain or branched halogenoalkyl having 1 to 4 carbon atoms and 1 to 9 identical or different halogen atoms, or phenyl which is optionally substituted by halogen, nitro, and in each case straight-chain or branched alkyl and/or halogenoalkyl each having 1 to 4 carbon atoms and in the case of halogenoalkyl having 1 to 9 identical or different halogen atoms, Ar represents phenyl, 2-pyridyl, 3-pyridyl or 4-pyridyl, which are each optionally substituted by cyano, nitro, halogen, or alkyl, alkoxy or alkoxycarbonyl which are each straight-chain or branched and each have 1 to 4 carbon atoms, in each case straight-chain or branched halogenoalkyl or halogenoalkoxy, each having 1 to 4 carbon atoms and 1 to 9 identical or different halogen atoms and/or the radical —S(O)$_z$—R⁶
in which R⁶ represents amino, alkyl, alkylamino, dialkylamino or halogenoalkyl, each being straight-chain or branched and having 1 to 4 carbon atoms in the individual alkyl parts and in the case of halogenoalkyl having 1 to 9 identical or different halogen atoms, x represents a number 0 or 1,
y represents a number 0 or 1,
z represents a number 0, 1 or 2.

3. A 1-arylpyrazole according to claim 1, in which
R¹ represents hydrogen or nitro,
R² represents hydrogen, methyl or ethyl,
R³ and R⁴ independently of one another each represent methyl, ethyl, n- or i-propyl, n-, i-, s- or t-butyl, chloromethyl, chloroethyl, chloropropyl, bromomethyl, bromoethyl, bromopropyl, dichloromethyl, trichloroethyl, trifluoroethyl, pentafluoroethyl or trichloromethyl, or phenyl which is optionally monosubstituted, disubstituted or trisubstituted by identical or different substituents from the group consisting of fluorine, chlorine, bromine, nitro, methyl, ethyl, n- or i-propyl and trifluoromethyl, Ar represents phenyl which is optionally monosubstituted to pentasubstituted by identical or different substituents or 2-pyridyl, which is optionally monosubstituted to tetrasubstituted by identical or different substituents, the phenyl and pyridyl substituents being selected from cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and the radical —S(O)$_z$—R⁶
in which R⁶ represents amino, methylamino, ethylamino, dimethylamino, diethylamino, fluorodichloromethyl, difluoromethyl, tetrafluoroethyl, trifluorochloroethyl, trichloromethyl, trichloroethyl, trifluoromethyl, methyl or ethyl, x represents a number 0 or 1,
y represents a number 0 or 1 and
z represents a number 0, 1 or 2.

4. A 1-arylpyrazole according to claim 1 in which
R¹ represents nitro,
R² represents hydrogen,
R³ and R⁴ independently of one another each represent methyl, ethyl, n- or i-propyl or phenyl;
Ar represents phenyl which is optionally substituted by identical or different substituents from the group consisting of fluorine, chlorine, bromine, methyl, ethyl, methoxy, ethoxy, trifluoromethyl, trifluoromethoxy, trifluoromethylthio, trifluoromethylsulphinyl and trifluoromethylsulphonyl, x represents a number 0 or 1 and
y represents the number 1.

5. A compound according to claim 1, wherein such compound is 5-(O,O-diethyl-phosphonylacetamido)-1-(2,6-dichloro-4-trifluoromethylphenyl)-4-nitropyrazole of the formula

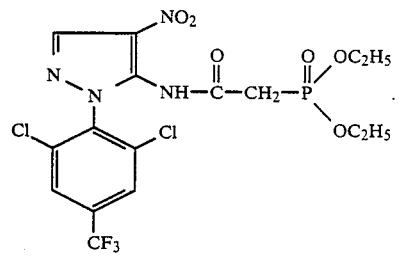

6. A compound according to claim 1, wherein such compound is 5-(O-ethylmethylphosphinoylacetamido)-1-(2,6-dichloro-4-trifluoromethylphenyl)-4-nitropyrazole of the formula

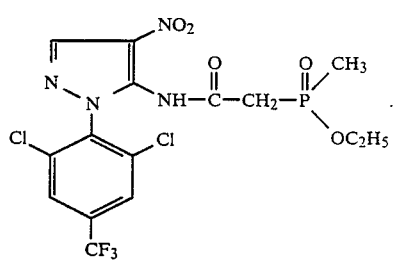

7. A compound according to claim 1, wherein such compound is 5-(O,O-dimethyl-phosphonylacetamido)-1-(2,6-dichloro-4-trifluoromethylphenyl)-4-nitropyrazole of the formula

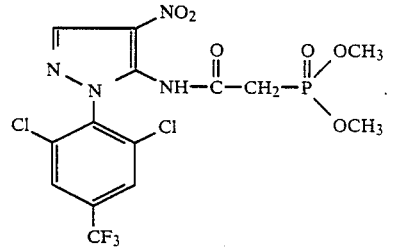

8. A compound according to claim 1, wherein such compound is 5-(O,O-dimethyl-phosphonylacetamido)-1-(2,3,6-trichloro-4-trifluoromethylphenyl)-4-nitropyrazole of the formula

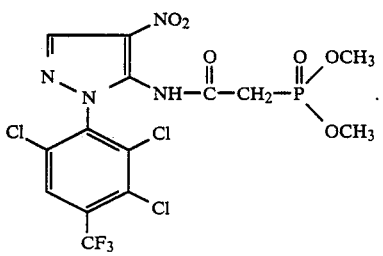

9. A compound according to claim 1, wherein such compound is 5-(O-ethylmethylphosphinoylacetamido)-1-(2,3,6-trichloro-4-trifluoromethylphenyl)-4-nitropyrazole of the formula

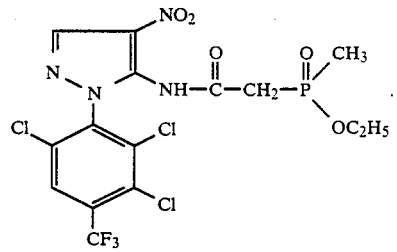

10. A herbicidal composition comprising a herbicidally effective amount of a 1-arylpyrazole according to claim 1 and a diluent.

11. A method of combating unwanted vegetation which comprises applying to such vegetation or to a locus from which it is desired to exclude such vegetation a herbicidally effective amount of a 1-arylpyrazole according to claim 1.

12. The method according to claim 11, wherein such compound is
   5-(O,O-diethyl-phosphonylacetamido)-1-(2,6-dichloro-4-trifluoromethylphenyl)-4-nitropyrazole,
   5-(O-ethylmethylphosphinoylacetamido)-1-(2,6-dichloro-4-trifluoromethylphenyl)-4-nitropyrazole,
   5-(O,O-dimethyl-phosphonylacetamido)-1-(2,6-dichloro-4-trifluoromethylphenyl)-4-nitropyrazole,
   5-(O,O-dimethyl-phosphonylacetamido)-1-(2,3,6-trichloro-4-trifluoromethylphenyl)-4-nitropyrazole or
   5-(O-ethylmethylphosphinoylacetamido)-1-(2,3,6-trichloro-4-trifluoromethylphenyl)-4-nitropyrazole.

* * * * *